United States Patent [19]

Tanaka et al.

[11] Patent Number: 5,389,547
[45] Date of Patent: Feb. 14, 1995

[54] PRETREATING REAGENT, PRETREATMENT METHOD, ASSAY WITH PRETREATED SAMPLES, ASSAY KIT AND METHOD OF DIAGNOSING INFECTIOUS DISEASES

[75] Inventors: Shigenori Tanaka; Hiroshi Tamura, both of Tokyo, Japan

[73] Assignee: Seikagaku Kogyo Kabushiki Kaisha (Seikagaku Corporation), Tokyo, Japan

[21] Appl. No.: 58,306

[22] Filed: May 10, 1993

[30] Foreign Application Priority Data

May 8, 1992 [JP] Japan .................................. 4-142010
Apr. 2, 1993 [JP] Japan .................................. 5-100426

[51] Int. Cl.$^6$ ............................................ G01N 33/00
[52] U.S. Cl. ................................... 436/94; 436/8; 436/63; 436/91; 436/174; 436/175; 435/4
[58] Field of Search .................... 436/17, 8, 69, 174, 436/175, 63, 94, 91; 435/184, 4

[56] References Cited

U.S. PATENT DOCUMENTS

| | | | |
|---|---|---|---|
| 4,414,336 | 11/1983 | Watanabe et al. | 436/502 |
| 4,476,093 | 10/1984 | Watanabe et al. | 422/61 |
| 4,495,294 | 1/1985 | Nakahara | 436/502 |
| 4,606,824 | 8/1986 | Chu et al. | 210/635 |
| 4,784,944 | 11/1988 | Kolde | 435/13 |
| 4,925,961 | 5/1990 | Ikeda et al. | 549/521 |
| 5,155,032 | 10/1992 | Tanaka et al. | 435/184 |
| 5,185,264 | 2/1993 | Makela | 436/18 |
| 5,250,436 | 10/1993 | Jamas et al. | 435/255.2 |

FOREIGN PATENT DOCUMENTS

| | | | |
|---|---|---|---|
| 0186476 | 7/1986 | European Pat. Off. | G01N 33/48 |
| 0513361A1 | 11/1992 | European Pat. Off. | . |
| 0513361 | 11/1992 | European Pat. Off. | G01N 33/579 |
| 126502 | 5/1989 | Japan | G01N 33/48 |
| 126503 | 5/1989 | Japan | G01N 33/48 |
| 1325043 | 8/1973 | United Kingdom | A61K 23/02 |
| 2059583 | 4/1981 | United Kingdom | . |
| WO9206382 | 4/1992 | WIPO | . |

OTHER PUBLICATIONS

K. Inada et al., Establishment of a New Perchloric Acid Treatment Method to Allow Determination of the Total Endotoxin Content in Human Plasma by the Limulus Test and Clinical Application, *Microbiol. Immunol.*, vol. 35, No. 4, pp. 303–314, 1991.

T. Obayashi et al., A new Chromogenic Endotoxin-Specific Assay Using Recombined Limulus Coagulation Enzymes and its Clinical Applications, *Clinica Chimica Acta*, vol. 149, No. 1, pp. 55–65, Jun. 1985.

H. Tamura et al., A New Sensitive Microplate Assay of Plasma Endotoxin, *Journal of Clinical Laboratory Analysis*, vol. 6, No. 4, pp. 232–238, 1992.

*Primary Examiner*—Donald E. Czaja
*Assistant Examiner*—Lien Tran
*Attorney, Agent, or Firm*—Sughrue, Mion, Zinn, Macpeak & Seas

[57] ABSTRACT

A reagent denatures or eliminates factors interfering with biochemical reactions by simple treatment without requiring separation of any denatured product precipitate. The reagent makes it possible to assay, in particular, β-glucan and endotoxin in blood-derived samples rapidly and efficiently with high sensitivity. The reagent includes a hexadimethrine compound and an alkali metal hydroxide or an alkali metal hydroxide as a main component. A method for assaying a substance specifically reacting with a Limulus reagent utilizing the reagent, an assay kit including at least the reagent and a Limulus reagent, and a method of diagnosing infectious diseases based on the results obtained by the assay method are also provided.

15 Claims, 1 Drawing Sheet

FIG. 1 ively is therefore a desirable assay method (the term "JP-A" used herein means an unexamined published Japanese patent application). However, accurate and precise assay is impossible since the reaction mixture volume on microplates is small and the assay is readily affected by turbidity of the reaction mixture, for instance.

PRETREATING REAGENT, PRETREATMENT METHOD, ASSAY WITH PRETREATED SAMPLES, ASSAY KIT AND METHOD OF DIAGNOSING INFECTIOUS DISEASES

FIELD OF THE INVENTION

The present invention relates to a reagent or reagent system for pretreating samples containing a factor or factors interfering with a biochemical reaction, a method of pretreating such samples, an assay method for the pretreated samples, a kit for use in said assay method, and a method of diagnosing infectious diseases based on said samples. In particular, it relates to a method of assaying (1→3)-$\beta$-D-glucan and endotoxin in biological samples, in particular blood-derived samples, containing a factor or factors interfering with the Limulus reaction, which uses a Limulus amebocyte lysate, and especially to a method of pretreating blood-derived samples obtained from patients suffering from fungal infection or infection with gram-negative bacteria and assaying (1→3)-$\beta$-D-glucan or endotoxin, respectively, with high accuracy to thereby effectively diagnose diseases caused by fungi or gram-negative bacteria.

BACKGROUND OF THE INVENTION

So far, biochemical assaying of selected target substances in biological sample has been widely used in association with clinical diagnosis. As a typical example of biochemical diagnosis, there may be mentioned the detection of fungi or gram-negative bacteria utilizing the Limulus reaction.

The Limulus reaction is a biochemical reaction in which a Limulus reagent is used.

Figure 1:
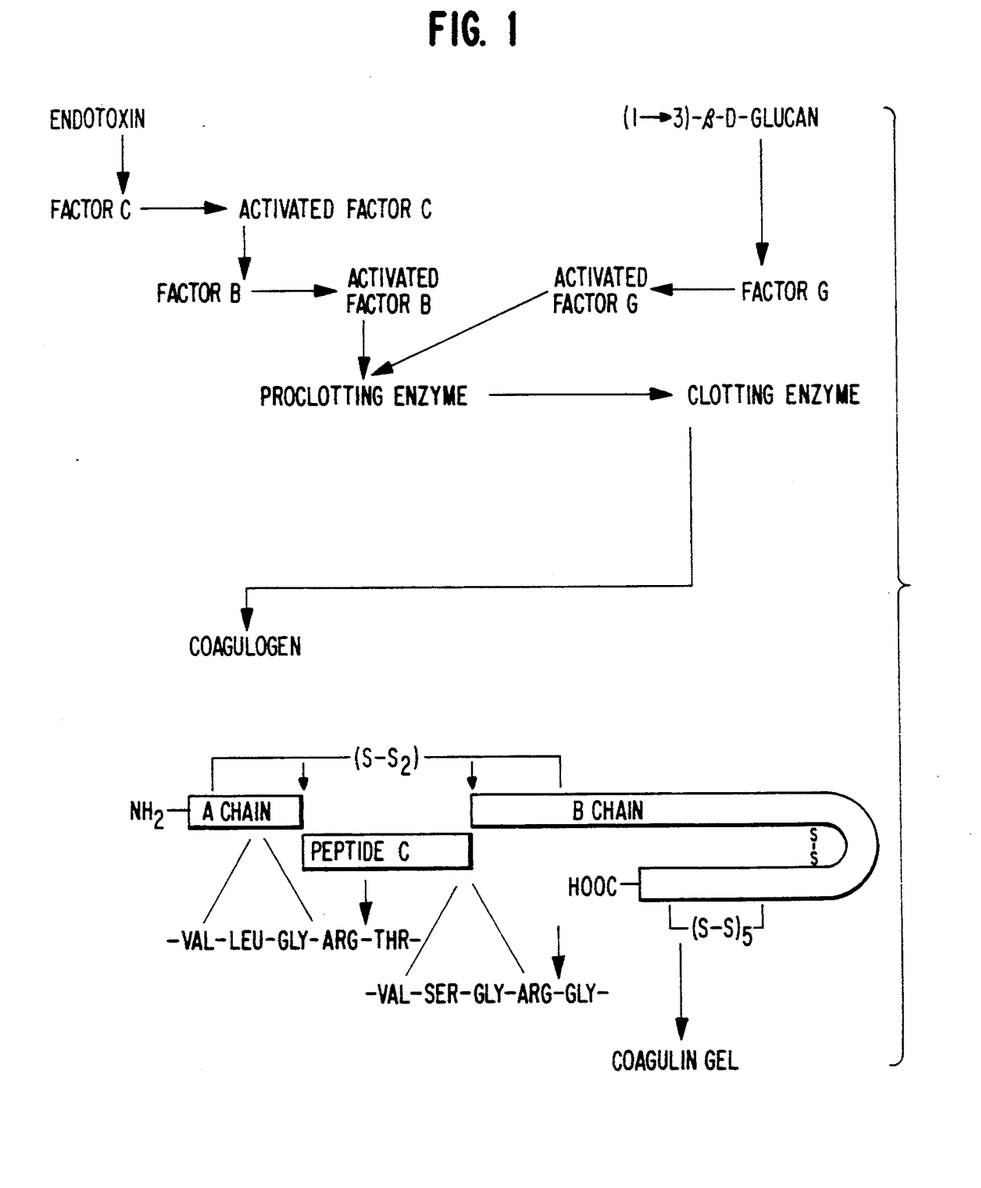
FIGURE 1 illustrates the reaction mechanisms of the cascade reactions of horseshoe crab amebocyte lysate as caused by $(1\rightarrow3)$-β-D-glucan and endotoxin, respectively.

In the horseshoe crab (Limulus) amebocyte lysate (hereinafter sometimes referred to as "lysate" for short) contained in the Limulus reagent, there coexist a cascade type coagulation system (factor C system), which reacts with endotoxin and is thereby activated, and a cascade type coagulation system (factor G system), which reacts with (1→3)-$\beta$-D-glucan (hereinafter sometimes referred to as "$\beta$-glucan") and is thereby activated (FIGURE 1). A method of specifically assaying endotoxin utilizing the former system alone and a method of specifically assaying $\beta$-glucan utilizing the latter system alone are known [Obayashi, T. et al., Clin. Chim. Acta, 149, 55-65 (1985)]. Patients with fungal infection show increased blood $\beta$-glucan levels while patients suffering from infection with gram-negative bacteria show increased blood endotoxin levels. It is also known that infections with fungi or gram-negative bacteria can be diagnosed by determining blood $\beta$-glucan or endotoxin levels.

Such methods of assaying $\beta$-glucan utilizing the factor G system and of assaying endotoxin utilizing the factor C system show very high detection sensitivity and therefore are suited for use in detecting both the substances mentioned above occurring in trace amounts in biological samples. In particular, their effectiveness in diagnosing deep fungal infections and infections caused by gram-negative bacteria has been studied and confirmed, and said methods are already in use to a certain extent in clinical testing.

Meanwhile, in determining $\beta$-glucan or endotoxin in biological samples, in particular blood samples utilizing the cascade reaction involving the factor G or factor C system of the lysate, respectively, said reaction is based on the reaction catalyzed by serine protease in the lysate and therefore various interfering factors contained in the samples (e.g. thrombin and factor Xa, which show similarity in action to clotting enzyme in the lysate and therefore behave as false positive factors, and $\alpha_2$-plasmin inhibitor, $\alpha_1$-antitrypsin and antithrombin III, which strongly inhibit the reaction, hence are false negative factors) must be deactivated or eliminated. Pretreatment is thus required. The prior art method so far employed for this purpose comprises preparing platelet rich plasma (PRP) by subjecting a blood samples to a specific treatment, further adding perchloric acid, incubating the resulting mixture at 37° C., removing the denatured product precipitate by centrifugation, collecting the supernatant and neutralizing the same with an alkali to give a test solution [Obayashi, T. et al., Clin. Chim. Acta, 149, 55-65 (1985)]. However, this method has problems. For instance, the procedure for separating the denatured product precipitate is complicated or troublesome, the whole procedure comprises a number of steps, and there is the risk of the reaction system being contaminated with a substance affecting said system during operation.

The prior art methods of pretreatment for assaying endotoxin or $\beta$-glucan are invariably carried out in test tubes and portions of the samples thus pretreated are transferred to other test tubes for performing the Limulus reaction. Furthermore, in conducting the assay by the synthetic substrate method, the end point technique has been generally employed which comprises converting, following the Limulus reaction, p-nitroaniline, formed upon substrate cleavage, to a red color through the diazotization reaction and measuring the absorbance. The end point technique is generally complicated in procedure and requires a rather long measurement time. A method by which a number of samples can be treated within a short period of time is demanded. Although the use of microplates in lieu of test tubes makes it possible to handle a large number of samples at a time, continuous automatic measurement by the end point technique is difficult to perform using microplates.

A kinetic assay method so far proposed (JP-A-3-220456) which can use such microplates and can determine the change of a substrate directly and automatically is therefore a desirable assay method (the term "JP-A" used herein means an unexamined published Japanese patent application). However, accurate and precise assay is impossible since the reaction mixture volume on microplates is small and the assay is readily affected by turbidity of the reaction mixture, for instance.

Furthermore, the method of pretreating samples for endotoxin assay is different from that for $\beta$-glucan assay since the reaction system to be used in the former assay is different from that to be used in the latter. If one and the same sample is to be assayed for both endotoxin and $\beta$-glucan, the sample requires different methods of pretreatment; this is very laborious and uneconomical. A pretreating reagent or reagent system which can be used in assaying both and with which only one pretreatment procedure is required is earnestly desired.

If a general-purpose pretreating reagent or reagent system is available with which various biological samples can be pretreated and rendered applicable to various biochemical reactions, such reagent or reagent system will eliminate the necessity of complicated pretreatment procedures differing from one another depending on the kind of assay method and the kind of biological sample and will make a very great contribution to biochemical research, diagnosis, etc. Such a pretreating reagent or reagent system is also desired.

SUMMARY OF THE INVENTION

An object of the present invention is to provide a pretreating reagent or reagent system, a pretreatment method, an assay method, an assay kit and a method of diagnosing infectious diseases by or with which β-glucan or endotoxin in blood-derived samples can be assayed rapidly and efficiently with very high sensitivity as a result of employment of a method capable of eliminating or denaturing factors interfering with biochemical reactions, for example factors interfering with the factor G system or factor C system reaction in the Limulus reaction, from said blood-derived samples containing said interfering factors by simple treatment without requiring isolation of the denatured product precipitate and without causing turbidity in biochemical reaction-based assaying.

The invention consists in a pretreating reagent system (hereinafter also referred to as "general-purpose pretreating reagent system") for pretreating a sample containing a factor or factors interfering with a biochemical reaction which comprises a hexadimethrine compound and an alkali metal hydroxide.

The pretreating reagent system of the invention is particularly suited for use in treating samples containing a factor or factors interfering with the Limulus reaction.

The invention provides a pretreatment method for treating a sample containing a factor or factors interfering with the Limulus reaction prior to detecting a substance detectable by the Limulus reaction as contained in said sample which comprises admixing the sample with the above-mentioned pretreating reagent system and incubating the mixture.

The invention provides a pretreating method for treating a sample containing a factor or factors interfering with the Limulus reaction prior to assaying $(1\rightarrow3)$-β-D-glucan in said sample utilizing the Limulus reaction which comprises admixing the sample with a pretreating reagent comprising an alkali metal hydroxide as a main component and incubating the mixture.

The invention provides a method of assaying a substance in a sample, which is specifically reactive with a Limulus reagent, utilizing the Limulus reaction which comprises pretreating the sample with the above-mentioned pretreatment methods, admixing the thus-treated sample with a Limulus reagent and allowing the reaction to proceed, and detecting the change of a substrate.

The invention provides an assay kit for assaying a substance specifically reacting with a Limulus reagent which comprises at least the following constituent reagents:

(A) The above-mentioned pretreating reagent system; and
(B) A Limulus reagent derived from a Limulus amebocyte lysate.

Lastly, the invention provides a method of diagnosing an infectious disease which comprises assaying a substance contained in a biological sample and specifically reactive with a Limulus reagent by the above-mentioned method, which detects the change of a substrate, and judging the sample as one derived from a living body suffering from an infectious disease when the assay value for said substance exceeds a certain level.

DETAILED DESCRIPTION OF THE INVENTION

In the following, the invention is described more specifically.

The "sample containing a factor or factors interfering with a biochemical reaction", to which the pretreating reagent system of the invention is to be applied, is a sample which possibly contain a target substance to be assayed based on said biochemical reaction and contains at least one interfering factor at a level enough to affect said biochemical reaction. A typical example of such sample is a biological sample, in particular a blood-derived sample. The blood-derived sample typically includes plasmas or sera obtained by treating blood samples collected from mammals, inclusive of humans, by a per se known method, or plasmas or sera containing proteases, protease inhibitors, blood-derived protein preparations, etc. The term "factor interfering with a a biochemical reaction" means a factor capable of reacting independently of the intended biochemical reaction (false positive factor) or a factor inhibiting the reaction in some or other step (false negative factor), typically including the above-mentioned factors contained in the blood.

For preparing plasma from blood, it is a general practice to add a blood coagulation inhibitor, such as heparin, to blood and centrifuge the same for precipitation of blood cells. When the centrifugation is performed at a low revolution rate (e.g. about 150×g), platelet rich plasma (PRP) is obtained whereas centrifugation at a high revolution rate (e.g. about 1,000×g) gives platelet poor plasma (PPP). When the blood-derived sample to serve as the assay target in the practice of the invention is plasma, it may be either PRP or PPP.

Sera are derived from blood samples by eliminating blood cells and some blood coagulation factors. Generally, they are prepared by allowing blood samples collected to stand in containers and removing the resulting blood clot.

Possible influences of interfering factors on biochemical reactions such as the Limulus reaction can be averted when the above-mentioned blood-derived samples and the like are treated with the pretreating reagent system of the present invention.

The "biochemical reaction" includes those reactions generally used for assaying biological substances, such as the Limulus reaction, antigen-antibody reactions, enzymatic reactions, etc.

The term "Limulus reaction" as used herein includes, within the meaning thereof, either one or both of the reaction between a factor C system fraction (fraction containing at least factors C and B and proclotting enzymes) of a lysate prepared by extraction of amebocytes (blood cells) of a horseshoe crab (the so-called horseshoe crab amebocyte lysate or Limulus amebocyte lysate) with a hypotonic solution or the like and endotoxin and the reaction of a factor G system fraction (fraction containing at least factor G and proclotting enzymes) of the lysate and β-glucan. The "Limulus reagent" and "Limulus reagent derived from horseshoe crab amebocyte lysate" each means a reagent for assaying endotoxin or β-glucan utilizing the above-mentioned Lumulus reaction and contains an ordinary horseshoe crab amebocyte lysate prepared from the hemolymph of a horseshoe crab, such as *Limulus polyphemus, Tachypleus tridentatus, Tachypleus gigas* or *Carcinoscorpius rotundicauda* by a per se known method [cf. e.g. J. Biochem., 80, 1011–1021 (1976)] and supplemented, as necessary, with the synthetic peptide substrate mentioned later herein. The "Limulus reagent specifically reacting with endotoxin" can be prepared by specifically inhibiting factor G in the above lysate or removing factor G by adsorption (e.g. WO 90/02951, U.S. Pat. No. 5,155,032, U.S. Pat. No. 5,179,006, WO 92/03736, WO 92/06381) or by fractionating factor C system components and reconstituting the same [e.g. JP-B-2-18080, JP-B-3-18080 (the term "JP-B" used herein means an examined published Japanese patent application); Obayashi, T. et al., Clin. Chim. Acta, 149, 55–65 (1985)]. The "Limulus reagent specifically reacting with β-glucan" can be prepared by specifically inhibiting factor C in the above lysate or removing said factor by adsorption (e.g. WO 91/19981, WO 92/16651) or by fractionating factor G system components, followed by reconstitution [Obayashi, T. et al., Clin. Chim. Acta, 149, 55–65 (1985)]. Therefore, the Limulus reagent for β-glucan assay is the one prepared such that the reaction system is not activated by endotoxin but is specifically activated by β-glucan. The Limulus reagent for endotoxin is the one prepared such that the reaction system is not activated by β-glucan but is specifically activated by endotoxin.

Any Limulus reagent, if it functions in the manner mentioned above, can be used in the practice of the invention. The method of production, composition and the like are not critical.

The factor interfering with said Limulus reaction in assaying β-glucan or endotoxin is, for example, a factor affecting the reaction involving factor G system or factor C system. The interfering factor is the false positive factor or false negative factor mentioned above which reacts independently of β-glucan or endotoxin in some or other step of the stepwise enzymatic reaction (cascade reaction), which is initiated by β-glucan or endotoxin, of the factor G and/or factor C system of the lysate, as shown in FIGURE 1.

In the following, the pretreating reagent system of the invention is described in further detail.

The general-purpose pretreating reagent system of the invention comprises at least a hexadimethrine compound and an alkali metal hydroxide.

The alkali metal hydroxide is the hydroxide of an alkali metal such as potassium, lithium or sodium, more specifically potassium hydroxide (KOH), lithium hydroxide (LiOH), sodium hydroxide (NaOH) or the like. Said pretreating reagent system generally takes the form of an aqueous solution containing one or a plurality of such alkali metal hydroxides. Most preferred alkali metal hydroxides are KOH and NaOH.

It is generally preferable to adjust the concentration of the alkali metal hydroxide in the pretreating reagent system so that the alkali metal hydroxide concentration in test solutions becomes 0.04 to 0.4 mole/liter.

The hexadimethrine compound to be used in the practice of the invention is preferably a hexadimethrine salt, for example a hexadimethrine halide. Preferred examples of the hexadimethrine halide are hexadimethrine bromide (generally called Polybrene), hexadimethrine chloride, etc. In the practice of the invention, however, the hexadimethrine compound is not limited to such halides but may include salts of hexadimethrine derivatives in which at least one hydrogen atom of hexadimethrine has been replaced by a substituent such as an alkyl group having from 1 to 6 carbon atoms, e.g. methyl, ethyl, etc. Most preferred hexadimethrine compound is hexadimethrine bromide.

The molecular weight of the hexadimethrine compound to be used in the practice of the invention is selected within the range of about 1,000 to 50,000, preferably 5,000 to 10,000. Said compound is used in a concentration, in the pretreating reagent system, within the range of 0.05 to 0.3%, preferably 0.1 to 0.2%, on the weight by volume basis. The amount of said compound is suitably adjusted depending on the biochemical reaction to which the sample should be subjected. This general-purpose pretreating reagent system may contain one or more optional chemical substances each in an appropriate amount. Those substances to be mentioned later herein as components of the pretreating reagent system applicable to the Limulus reaction can also be used.

Said general-purpose pretreating reagent system, when applicable to the Limulus reaction, for instance, can be used for assaying endotoxin, assaying β-glucan or assaying both. It is possible to finely adjust the amount of the hexadimethrine compound and the amounts of other components depending on the kind of assay, as necessary.

Thus, the present invention can provide a pretreating reagent system for use in assaying both endotoxin and β-glucan (hereinafter also referred to as dual-purpose pretreating reagent system) which comprises at least the above-mentioned alkali metal hydroxide and hexadimethrine compound.

The alkali metal hydroxide is considered to have the function of denaturing interfering factors as its main function, while the hexadimethrine compound is effective in reducing the turbidity of the test sample or, in other words, in preventing nonspecific turbidity increase presumably due to neutral fats and lipoproteins but will not interfere with either of both the reaction systems. When samples are treated singly with the dual-purpose pretreating reagent system containing both the substances, said samples can be assayed in each reaction system.

A specific component other than said two components can be added to the dual-purpose pretreating reagent system of the invention for further improving the precision of assay. As such component, there may be mentioned, for instance, an amino or imino compound, bicine [chemical name: N,N-bis(2-hydroxyethyl)glycine; one of Good's buffers] and the like.

The amino or imino compound includes amino acids, imino acids, polyamino acids, polyethyleneimine, amino-containing nucleic acid bases, and salts of these. Specific examples are histamine dihydrochloride, L-histidine dihydrochloride, poly-L-histidine hydrochloride (molecular weight: 15,000 to 50,000), poly-L-lysine hydrochloride (molecular weight: 2,000 to 70,000), poly-L-arginine hydrochloride (molecular weight: 5,000 to 150,000), polyethyleneimine (molecular weight: 1,000 to 70,000), adenine hydrochloride and cytosine hydrochloride.

These amino or imino compounds are used in a concentration, in the pretreating reagent system, within the range of 0.03 to 0.3% (weight/volume).

Bicine, is used in a concentration, in the pretreating reagent system, within the range of 0.005 to 0.05 mole/liter, preferably 0.02 to 0.05 mole/liter.

The dual-purpose pretreating reagent system of the invention can also be used as an intermediate reagent for preparing an exclusive-use pretreating reagent system for endotoxin assay and/or an exclusive-use pretreating reagent system for $\beta$-glucan assay.

The pretreating reagent system to be used in assaying endotoxin in samples utilizing the Limulus reaction (pretreating reagent system for endotoxin assay) comprises a hexadimethrine compound and an alkali metal hydroxide, as mentioned above, and which further contains at least a nonionic or anionic surfactant and an alkaline earth metal halide.

The nonionic surfactant is not particularly limited in kind but includes, among others, polyoxyethylene ethers, polyoxyethylene sorbitan alkyl esters and alkyl glucoside.

The polyoxyethylene ethers are polyoxyethylene p-tertiary-octyl(or isooctyl)phenyl ether (polymerization degree: 8 to 40), polyoxyethylene 4-tertiary-octyl(or isooctyl)cyclohexyl ether (polymerization degree: 8 to 40), polyoxyethylene p-nonylphenyl ether (polymerization degree: 9 to 15), polyoxyethylene heptamethylhexyl ether (polymerization degree: 10 to 20), polyoxyethylene dodecyl ether (polymerization degree: 10 to 29) and the like, inclusive of such commercial products as Triton series surfactants (octoxynol; polyoxyethylene p-t-octylphenyl ethers), Brij series surfactants (polyoxyethylene alkyl ethers) and Emulgen series surfactants (polyoxyethylene nonylphenyl ethers).

As the alkyl glucosides, there may be mentioned n-heptyl ($\alpha$- or $\beta$-)D-glucopyranoside, n-octyl ($\alpha$- or $\beta$-)D-glucopyranoside, n-nonyl ($\alpha$- or $\beta$-)D-glucopyranoside, n-decyl ($\alpha$- or $\beta$-)D-glucopyranoside, n-dodecyl ($\alpha$- or $\beta$-)D-glucopyranoside and the like.

As the polyoxyethylene sorbitan alkyl esters, there may be mentioned polyoxyethylene sorbitan (polymerization degree: about 20) monolaurate, monopalmitate, monostearate, monooleate and trioleate and the like, including such commercial products as Tween series surfactants.

Examples of the Triton series surfactants are Triton X-100, X-114, X-102, X-165, X-305, X-405, Igepal CA-630, Neutronyx 605, Conco NIX-100 and Nonidet P-40. Examples of the Brij series surfactants are Brij 35 and 58. Examples of Emulgen series surfactants are Emulgen 911 and 913. Tween 20, 40, 60, 80 and 85 are examples of the Tween series surfactants. Most preferred nonionic surfactants are Triton series and Tween series surfactants.

The anionic surfactant includes alkyl sulfates, such as dodecyl sulfates, and alkyl benzene sulfonates. Specific examples of the dodecyl sulfates are sodium dodecyl sulfate, lithium dodecyl sulfate and potassium dodecyl sulfate. Most preferred anionic surfactant is sodium dodecyl sulfate.

As the alkaline earth metal halide, there may be mentioned calcium chloride, magnesium chloride, strontium chloride, and the like. Most preferred alkaline earth halide is calcium chloride.

The proportions of the hexadimethrine compound and alkali metal hydroxide in this pretreating reagent system for endotoxin assay can be adjusted in substantially the same respective ranges as mentioned above for the general-purpose pretreating reagent system. The surfactant is used in a concentration, in the pretreating reagent system, within the range of 0.04 to 0.4% (weight/volume), and the alkaline earth metal halide in a concentration, in the pretreating reagent system, within the range of 0.005 to 0.05 mole/liter.

The pretreating reagent system for endotoxin assay of the invention may further contain optional additional components. Thus, for instance, the above-mentioned amino or imino compounds, bicine and the like can be used in a concentration within substantially the same range as mentioned above for the dual-purpose pretreating reagent system.

The pretreating reagent system for use in assaying (1→3)-$\beta$-D-glucan in samples utilizing the Limulus reaction (pretreating reagent system A for $\beta$-glucan assay) comprises a hexadimethrine compound and an alkali metal hydroxide, as mentioned above, and which further contains an alkali metal halide.

The alkali metal halide is, for example, sodium chloride, potassium chloride or lithium chloride. Most preferred alkali metal halides are potassium chloride and sodium chloride. This alkali metal halide is considered to be capable of inhibiting the adsorption of $\beta$-glucan by blood components.

The proportions of the hexadimethrine compound and alkali metal hydroxide in the pretreating reagent system A for $\beta$-glucan assay of the invention can be adjusted within substantially the same respective ranges as mentioned above for the dual-purpose pretreating reagent system. The alkali metal halide is used in a concentration, in the pretreating reagent system, within the range of 0.05 to 0.5 mole/liter.

The pretreating reagent system A for $\beta$-glucan assay of the invention may further contain optional additional components. Thus, for instance, the above-mentioned amino or imino compounds, bicine and the like can be used within substantially the same concentration range as mentioned above for the dual-purpose pretreating reagent system.

The invention further provides the pretreating reagent system for $\beta$-glucan assay (pretreating reagent system B for $\beta$-glucan assay) which comprises the above-mentioned alkali metal hydroxide as a main component. Other additives may be added, as necessary, to this pretreating reagent system B. As such additives, there may be mentioned, for instance, substances capable of inhibiting the factor G system cascade reaction resulting from adsorption of $\beta$-glucan by blood components, or stabilizing the reaction system, or improving the reproducibility. Preferred examples of such additives are alkali metal halides as mentioned above.

The above-mentioned various pretreating reagent systems of this invention each may be stored as a plurality of solutions which are to be mixed up immediately prior to use. In particular, those components which, when mixed up in advance, may cause turbidity or undergo decomposition should preferably be stored in separate solutions.

For example, when the alkali metal hydroxide, the alkaline earth metal halide and/or nonionic surfactant are mixed and stored for a long period of time, the mixture becomes turbid. Thus, these components are preferably mixed immediately prior to the pretreatment or at the time of the pretreatment. It is particularly preferred that potassium hydroxide, calcium chloride and Triton X-100 are separately stored. The component(s) is stored in an aqueous solution such as distilled water. The pH value of the solution is adjusted so as to be pH 10–13 upon use.

Samples can be treated with the pretreating reagent system mentioned above basically by admixing the samples with said reagent system, followed by warming (incubation). If desired, the incubation may be performed with stirring, shaking or the like. The treatment temperature on this occasion is suitably selected generally within the range of 25° to 70° C., preferably 37° to 56° C., and the treatment time within the range of 5 to 40 minutes, preferably 5 to 20 minutes, depending on the biochemical reaction to be applied after the pretreatment and/or the kind of sample. In cases where the assay target substance is common, for instance, the pretreating reagent systems may be combinedly used in admixture in some instances.

This pretreatment method is suitably used when the sample is a blood-derived one.

When the substance detectable by the Limulus reaction is endotoxin, the pretreating reagent system is the one for endotoxin. When the substance detectable by the Limulus reaction is (1→3)-β-D-glucan, the pretreating reagent system is the pretreating reagent system A or B for β-glucan assay.

The assay of a substance specifically reacting with the Limulus reagent, namely endotoxin or β-glucan, in samples utilizing the Limulus reaction can be performed by admixing the samples treated with the pretreating reagent system of the invention with a Limulus reagent derived from horseshoe crab amebocyte, incubating and then detecting the change of a substrate. The pretreated mixture can be directly subjected to the Limulus reaction without subjecting to centrifugation or neutralization. The assay method utilizing the Limulus reaction according to the present invention can be carried out by adding a Limulus reagent to the pretreated mixture, incubating the reaction mixture at about 37° C. and at pH 7-9 for an appropriate time, detecting the change of a substance by an appropriate method suited for the substrate used and calculating the content of endotoxin or β-glucan in the sample from the calibration curve which has been prepared using a standard endotoxin or β-glucan solution.

In this case, for assaying endotoxin, it is necessary to admix samples treated with the above-mentioned dual-purpose pretreating reagent system or pretreating reagent system for endotoxin assay with a Limulus reagent containing factor C system components at least reactive with endotoxin and allow the reaction to proceed and it is very preferable to select, as said Limulus reagent, one specifically reactive only with endotoxin. As such Limulus reagent, there may be mentioned those which contains factor C system components, with the factor G system components having been eliminated or being inhibited.

On that occasion, the dual-purpose pretreating reagent system and pretreating reagent system for endotoxin assay may be used combinedly in some instances.

For assaying β-glucan, it is necessary to admix samples treated with the above-mentioned dual-purpose pretreating reagent system or pretreating reagent system A or B for β-glucan assay (these three pretreating reagent systems may be used combinedly in admixture) with a Limulus reagent containing factor G system components reactive at least with β-glucan and allow the reaction to proceed and it is very preferable to select, as said Limulus reagent, one specifically reacting only with β-glucan. As such Limulus reagent, there may be mentioned those containing factor G system components, with the factor C system components having been eliminated or being inhibited.

Accordingly, the reaction mixture for assaying endotoxin or β-glucan is preferably adjusted to a pH around the optimal pH for the factor G system or factor C system. Thus, the pH is generally adjusted to 7 to 9 with a conventional buffer solution as desired. As shown in the example section appearing later herein, it has been established that the false positive factor and/or false negative factor deactivated by the pretreatment according to the invention will not resume its activity. Conversely, it is presumably due to the action of the buffer that the pretreating reagent system will not adversely affect the reactivity of each component in the factor G system or factor C system in mixing up the sample solutions treated with the pretreating reagent system and containing a relatively high concentration of basic substance and the Limulus reagent.

For assaying β-glucan or endotoxin in each sample solution pretreated in the above manner, measurement of the amidase activity or protease activity, against a substrate, of clotting enzymes formed in said reaction mixture by activation through the cascade reaction involving the factor G or factor C system of the lysate, as mentioned above and shown in FIGURE 1, is carried out by a per se known technique. The substrate, which may be either a synthetic one or a natural one, is a substrate which can be hydrolyzed by clotting enzymes to give a readily detectable product and thus cause a change based on enzymatic reactions in the reaction mixture which change can be measured either qualitatively or quantitatively.

Thus, for instance, amidase activity measurement can be performed by contacting a reaction system containing a lysate for β-glucan or endotoxin assay and a synthetic peptide substrate with the sample solutions. Examples of such synthetic peptide substrate (synthetic peptide for a substrate) are those peptides derived from peptides capable of serving as substrates for the above-mentioned clotting enzymes (e.g. methoxycarbonyl-D-hexahydrotyrosyl-Gly-Arg; N-terminally protected peptides having such sequence as Leu-Gly-Arg, Ile-Glu-Ala-Arg or the like) by substitution in the C-terminal arginine carboxyl group with a chromogenic residue [e.g. the residue of p-nitroaniline, p-(N,N-diethylamino)aniline, p-(N-ethyl-N-β-hydroxyethyl)aniline, etc.], a fluorescence emitting residue (e.g. the residue of 7-aminomethylcoumarin, etc.), a luminescent residue or ammonia via amide bonding. Thus, amidase activity measurement can be performed by assaying the reaction products (p-niroaniline, ammonia, etc.) formed when the clotting enzymes act on these synthetic peptide substrates. More specifically, the synthetic peptide substrate mentioned above is allowed to coexist in the reaction system containing a sample solution pretreated in the above manner and the factor G system components or factor C system components of a lysate and thereby allow the reaction(s) (cascade reaction and, as necessary, a reaction for converting the product to some other coloring matter or the like) to proceed. The coloring matter, fluorescent substance, luminescent substance or ammonia thus formed can be measured by techniques generally employed in assaying endotoxin and using, for instance, a spectrophotometer (JP-B-63-26871, JP-B-3-66319, etc.), fluorophotometer, chemiluminescence measuring device, or electrode for detecting ammonia (JP-A-62-148860), respectively.

In particular, the pretreating reagent system of the invention is effectively used in pretreating on microplates, which is to be followed by a biochemical reaction such as the Limulus reaction. Said reagent system is particularly suited for use in performing kinetic assays by two wavelength simultaneous photometry and therefore makes it possible to assay the target substance as desired rapidly and exactly.

On the other hand, for determining the protease activity of clotting enzymes, use can be made, for example, of the methods employed for endotoxin assay (JP-B-4-14310 etc.) which comprise measuring or judging the coagulin gel formation reaction resulting from the action of clotting enzymes formed by the cascade reaction on a coagulogen, which is a natural substrate for clotting enzyme, contained in a Limulus reagent for $\beta$-glucan assay or Limulus reagent for endotoxin assay using an appropriate device (e.g. turbidimeter, viscometer, etc.) or by the eye. The Limulus reagent to be used in the above reaction is preferably one (for endotoxin) prepared from the lysate by specifically inhibiting factor G thereof or eliminating said factor by adsorption or one (for $\beta$-glucan) prepared from the lysate by specifically inhibiting factor C or eliminating said factor by adsorption. While these Limulus reagents generally contain coagulogen, it is of course possible to add coagulogen from a separate source.

The $\beta$-glucan assay method of the invention is useful in the early diagnosis of fungal infections, in particular deep fungal infections, which are very difficult to diagnose, and the endotoxin assay method is useful in the early diagnosis of infections with gram-negative bacteria.

For diagnosing fungal infections, blood-derived samples collected from patients suspected of fungal infection are treated with the pretreating reagent system of the invention and then subjected to the $\beta$-glucan assay as described above. When the blood $\beta$-glucan level in a patient is above a certain limit (normal level), the patient can be judged to be suffering from a fungal infection.

Similarly, for diagnosing infections with gram-negative bacteria, blood-derived samples collected from patients suspected of the bacterial infection are treated with the pretreating reagent of the invention and then subjected to the endotoxin assay as described above. When the blood endotoxin level is above a certain limit (normal level), the patient can be judged to be suffering from an infection with gram-negative bacteria.

In accordance with the present invention, the desired assay kit can be constituted by suitably combining at least one reagent system (A) selected from among the above-mentioned dual-purpose pretreating reagent system, pretreating reagent system for endotoxin assay and pretreating reagent system A or B for $\beta$-glucan assay with at least one of the above-mentioned Limulus reagent (B) for endotoxin assay and for $\beta$-glucan assay.

The kit of the invention may further comprise another or other optional constituent reagents as necessary. As such reagents, there may be mentioned a standard reagent containing an appropriate known amount of endotoxin or $\beta$-glucan, distilled water for blank test, a buffer solution for dissolving reagents and for carrying out the reaction, and so forth.

For specifically assaying endotoxin, it is preferable that the Limulus reagent (B) is one specifically reacting with endotoxin. The kit preferably comprises, as a further constituent reagent, (C) a standard reagent containing a certain known amount of endotoxin.

For specifically assaying $\beta$-glucan, it is preferable that the Limulus reagent (B) is one specifically reacting with $\beta$-glucan. The kit preferably comprises, as a further constituent reagent, (D) a standard reagent containing a known amount of $\beta$-glucan.

As examples of said buffer solution, there may be mentioned Good's buffer solutions [e.g. HEPES (N-2-hydroxyethylpiperazine-N'-2-ethanesulfonic acid) buffer solution etc.], Tris-hydrochloride buffer solution, and the like.

The following examples are further illustrative of the present invention but are by no means limitative of the scope thereof.

EXAMPLE 1-1

Recovery of $\beta$-Glucan added to PRP (Influence of KOH Concentration in Pretreating Reagent System)

Blood (2 ml) collected from each healthy subject with 5 units of heparin per ml of blood added was centrifuged at 150×g for 10 minutes to give a platelet rich plasma (PRP).

To 190 $\mu$l of this PRP sample was added 10 $\mu$l of a solution of a *Poria cocos*-derived $\beta$-glucan preparation [pachyman; prepared by the method of Saito et al., Agric. Biol. Chem., 32, 1261–1269 (1968)] (1.0 ng/ml) in a 0.01M aqueous solution of sodium hydroxide (NaOH). After thorough mixing, the mixture was distributed in 5-$\mu$l portions into wells of a $\beta$-glucan-free microplate (Toxipet Plate 96F, a trade name of the product distributed by Seikagaku Corporation) and aqueous solutions of potassium hydroxide (KOH) [pretreating reagent] with concentrations selected within the range of 0 to 1.0 mole/liter were respectively added in 20-$\mu$l portions to the wells (the KOH concentrations in the resulting mixtures in the wells being 0 to 0.8 mole/liter) and, after 10 minutes of incubation at 37° C., said mixtures were used as test solutions.

$\beta$-Glucan occurring in each test solution was assayed by the following method. A lyophilized reagent system for $\beta$-glucan assay by the synthetic chromogenic substrate method which contains factor G system components prepared from a horseshoe crab amebocyte lysate by the method of Obayashi, T. et al. [Clin. Chim. Acta, 149, 55–65 (1985)] and a synthetic chromogenic substrate [Boc-Leu-Gly-Arg-pNA (p-nitroanilide)] was used. (Said assay reagent system is hereinafter referred to as "G test".) To 25 $\mu$l of each test solution were added 50 $\mu$l of a solution of G test in 0.2 mole/liter Tris-hydrochloride buffer (pH 8.0) and 50 $\mu$l of distilled water. The mixture was incubated at 37° C. for 30 minutes for allowing the reaction to proceed, then diazo coupling was performed by adding 50 $\mu$l of 0.04% (weight/volume) sodium nitrite (in 1 mole/liter hydrochloric acid), 50 $\mu$l of 0.3% (weight/volume) ammonium sulfamate and 50 $\mu$l of 0.07% (weight/volume) N-1-naphthylethylenediamine dihydrochloride [in 14% (weight/volume) N-methyl-2-pyrrolidone solution] in that order, and assaying was made by measuring the absorbance at 545 nm using a microplate reader (545–630 nm; reference wavelength: 630 nm).

Table 1 shows the $\beta$-glucan recovery percentages obtained by varying the KOH concentration in the pretreating reagent system to thereby adjust the KOH concentration in the test solution, together with the measurement results (absorbance values) for the PRP samples pretreated under the same conditions without addition of β-glucan.

TABLE 1

| Test solution | KOH concentration | Absorbance of test solution without addition of β-glucan | Recovery of β-glucan (%) |
|---|---|---|---|
| PRP (+ β-glucan + KOH) | 0.000 | 0.024 | 0 |
| | 0.016 | 0.025 | 3 |
| | 0.032 | 0.029 | 65 |
| | 0.040 | 0.030 | 90 |
| | 0.060 | 0.030 | 100 |
| | 0.080 | 0.030 | 100 |
| | 0.160 | 0.030 | 100 |
| | 0.240 | 0.029 | 100 |
| | 0.320 | 0.028 | 95 |
| | 0.400 | 0.027 | 92 |
| | 0.600 | 0.027 | 70 |
| | 0.800 | 0.026 | 65 |
| Control | 0.000 | 0.025 | 100 |

In Table 1, the KOH concentration (moles/liter) is the concentration in the test solution in the step of treating PRP, and the absorbance of the test solution containing no added β-glucan is the absorbance of PRP pretreated without addition of β-glucan as measured at 545–630 nm.

The recovery of β-glucan is the percent recovery of β-glucan added to the test solution (PRP pretreated following addition of β-glucan thereto), with the measured value for the corresponding control being taken as 100%. For obtaining said control or reference value, physiological saline for injection was used in lieu of PRP, and distilled water for injection in lieu of the pretreating reagent, and the assay was conducted with and without addition of β-glucan.

The data shown in Table 1 indicate that treatment with distilled water for injection alone does not result in detection of β-glucan at all but that the recovery markedly increases with the increase in the KOH concentration in test solution. Furthermore, it is evident that when the KOH concentration is above 0.6 mole/liter or below 0.03 mole/liter, the recovery of β-glucan is low but that when said concentration is about 0.04 to 0.4 mole/liter, the effects of the false positive factor and inhibitory factor (false negative factor) in the factor G system reaction can be counteracted, hence the true β-glucan levels in PRP can be detected with high reliability and reproducibility.

Thus, when the absorbance of PRP pretreated without addition of β-glucan is equal to the value obtained with the control without addition of β-glucan, this means that the factor G system reaction false positive factor in PRP was completely denatured. When the β-glucan recovery in an example in which the assay was performed with addition of β-glucan (PRP pretreated following addition of β-glucan) is 100%, this means that the factor G system reaction inhibiting factor (false negative factor) in PRP was wholly denatured. Therefore, the ideal conditions are those under which these interfering factors both can be denatured and deactivated, namely the conditions under which the measured value for PRP pretreated without addition of β-glucan is substantially identical with the control value and under which the β-glucan recovery for PRP pretreated with addition of β-glucan is nearly 100%.

As the results shown in Table 1 indicate, it is a necessary condition for meeting the ideal conditions mentioned above that the KOH concentration in test solution should be 0.04 to 0.4 mole/liter.

EXAMPLE 1-2

Recovery of β-Glucan added to PRP (Influence of NaOH Concentration in Pretreating Reagent System)

To 190 μl of each PRP sample prepared by the same means as used in Example 1-1 was added 10 μl of a solution of the same β-glucan preparation as used in Example 1-1 (pachyman) in a 0.01M aqueous solution of NaOH (1.0 ng/ml). After thorough mixing, the mixture was distributed in 5-μl portions into wells of Toxipet Plate 96F, and aqueous solutions of NaOH with concentrations selected within the range of 0 to 0.8 mole/liter were respectively added in 20-μl portions to the wells (the NaOH concentrations in the resulting mixtures becoming 0 to 0.8 mole/liter) and, after 10 minutes of incubation at 37° C., said mixtures were used as test solutions.

β-Glucan occuring in each test solution was assayed in the same manner as in Example 1-1 using G test.

Table 2 shows the β-glucan recovery percentages obtained by varying the NaOH concentration, together with the measurement results (absorbance values) for the PRP samples pretreated under the same conditions without addition of β-glucan.

TABLE 2

| Test solution | NaOH concentration (mole/liter) | Absorbance of test solution without addition of β-glucan | Recovery of β-glucan (%) |
|---|---|---|---|
| PRP (+ β-glucan) + NaOH | 0.000 | 0.024 | 0 |
| | 0.016 | 0.024 | 2 |
| | 0.032 | 0.029 | 55 |
| | 0.040 | 0.030 | 88 |
| | 0.060 | 0.030 | 100 |
| | 0.080 | 0.030 | 100 |
| | 0.160 | 0.030 | 100 |
| | 0.240 | 0.030 | 100 |
| | 0.320 | 0.028 | 94 |
| | 0.400 | 0.028 | 90 |
| | 0.600 | 0.027 | 75 |
| | 0.800 | 0.026 | 72 |
| Control | 0.000 | 0.025 | 100 |

In Table 2, the NaOH concentration (moles/liter) is the concentration in the test solution in the step of treating PRP, and the absorbance of the test solution containing no added β-glucan is the absorbance of PRP pretreated without addition of β-glucan as measured to 545–630 nm. The recovery of β-glucan is the precent recovery of β-glucan added to the test solution (PRP pretreated following addition of β-glucan thereto), with the measured value for the corresponding control being taken as 100%. For obtaining said control or reference value, physiological saline for injection was used in lieu of PRP, and distilled water for injection in lieu of the pretreating reagent, and the assay was conducted with and without addition of β-glucan.

The data shown in Table 2 indicate that treatment with distilled water for injection alone does not result in detection of β-glucan at all but that the recovery markedly increases with the increase in the NaOH concentration in test solution.

The results shown in Table 2 revealed that when an aqueous NaOH solution having a concentration such that the test solution acquires an NaOH concentration of 0.04 to 0.4 mole/liter is used as the pretreating reagent, the effects of the false positive and false negative factors can be neutralized, as in Example 1-1 where aqueous KOH solutions were used as the pretreating reagent.

EXAMPLE 1-3

Recovery of β-Glucan added to Sera (Influence of Treatment Time)

Blood (3 ml) collected from each healthy subject without using any anticoagulant was allowed to stand at 4° C. for 1 hour and then centrifuged at 1,000×g for 10 minutes to give a serum.

To 190 µl of this serum sample was added 10 µl of an aqueous solution containing 10 pg of the same β-glucan preparation (pachyman) as used in Example 1-1. The mixture was distributed in 5-µl portions into wells of Toxipet Plate 96F and a 0.1 mole/liter aqueous KOH solution [pretreating reagent] was added in 20-µl portions to the wells. After each predetermined period of incubation at 37° C., the resulting mixtures were used as test solutions.

β-Glucan added to each test solution in the above manner was assayed in the same manner as in Example 1-1.

The measurement results obtained after various periods of incubation are shown in Table 3 in the same manner as in Example 1-1.

TABLE 3

| Test solution | Time of warming (minutes) | Absorbance of test solution without addition of β-glucan | Recovery of β-glucan (%) |
|---|---|---|---|
| Serum | 0 | 0.025 | 4 |
| (+ β- | 5 | 0.026 | 94 |
| glucan) | 10 | 0.031 | 100 |
| + KOH | 15 | 0.031 | 100 |
| | 20 | 0.032 | 100 |
| | 30 | 0.031 | 100 |
| | 40 | 0.030 | 96 |
| | 60 | 0.028 | 73 |
| Control | | 0.025 | 100 |

It is seen from Table 3 that when the incubation time is zero, namely when the assay is performed with the test solution just after addition of the pretreating agent, the β-glucan recovery is very low. On the contrary, when test solutions were subjected to assaying after 5 to 40 minutes of incubation, β-glucan could be assayed quantitatively. Thus, it is evident that when pretreatment is performed under such conditions, the false positive factor and inhibitory factor can be denatured and the true levels of β-glucan in sera can be detected accurately and with high reliability and reproducibility.

EXAMPLE 1-4

Recovery of β-Glucan added to PPP (Influence of Pretreatment Temperature)

Blood (2 ml) collected from each healthy subject with heparin added in an amount of 5 units per milliliter of blood was centrifuged at 1,000×g for 10 minutes to give platelet poor plasma (PPP).

To 190 µl of this PPP sample was added 10 µl of a 0.01 mole/liter aqueous NaOH solution containing 40 pg of *Alcaligenes faecalis* var. *myxogenes* IFO 13140-derived β-glucan (curdlan; distributed by Wako Pure Chemical Industries, Ltd.), and the mixture was distributed in 5-µl portions into wells of Toxipet Plate 96F. To each well was added 20 µl of a 0.1 mole/liter KOH solution. After 10 minutes of incubation at various predetermined temperatures, the mixtures were used as test solutions.

β-Glucan added to each of the above test solutions was assayed by the same means as used in Example 1-1.

The results of measurement at various temperatures are shown in Table 4 in the same manner as in Example 1-1.

TABLE 4

| Test solution | Treatment temperature (°C.) | Absorbance of test solution without addition of β-glucan | Recovery of β-glucan (%) |
|---|---|---|---|
| PPP | 4 | 0.025 | 12 |
| (+ β- | 20 | 0.029 | 84 |
| glucan) | 25 | 0.030 | 93 |
| + KOH | 37 | 0.031 | 100 |
| | 45 | 0.031 | 100 |
| | 56 | 0.031 | 100 |
| | 70 | 0.027 | 91 |
| Control | | 0.025 | 100 |

As shown in Table 4, the recovery of β-glucan was low when the treatment temperature was 4° C. whereas the β-glucan added to PPP could be detected quantitatively when the treatment was performed at a temperature of 25° C. or above.

EXAMPLE 1-5

Assay of PRP Samples from Patients with Fungal Infection

Blood was collected from each of several patients suspected of fungal infection by the procedure of Example 1-1 and a PRP sample was prepared therefrom. A 5-µl portion of said sample was placed in a well of Toxipet Plate 96F, and 20 µl of a 0.1 mole/liter aqueous NaOH solution was further added to the well. After 10 minutes of incubation at 37° C., the mixture in the well was used as a test solution. The mixture was reacted with G-Test by the same means as used in Example 1-1 and the absorbance was measured. Using known amounts of the same reagent curdlan as used in Example 1-4 as a standard reagent, a calibration curve was constructed separately and, based on this curve, the β-glucan content in each test solution was determined. The results thus obtained are shown in Table 5.

TABLE 5

β-Glucan levels in plasma samples (PRP) from patients with opportunistic profound fungal infection

| No. | Disease | PRP β-glucan | Seroculture | Clinical symptom | Outcome |
|---|---|---|---|---|---|
| 1 | ALL | 357.7 pg/ml | (+) | *Candida albicans* isolated | Died |
| 2 | AML | 27.4 | (+) | *Candida tropicalis* isolated | Died |
| 3 | AIHA | 594.6 | (+) | *Cryptococcus neoformans* isolated | Surviving |
| 4 | ALL | 60.6 | (−) | Systemic aspergillosis (autopsy) | Died |
| 5 | ALL | 92.5 | (−) | Improvement after miconazole | Surviving |
| 6 | AML | 46.1 | (−) | Improvement after miconazole | Surviving |

ALL: Acute lymphatic leukemia; AML: Acute myelocytic leukemia; AIHA: Autoimmune hemolytic anemia.

As shown in Table 5, β-glucan was detected in high concentrations in all the cases (No. 1 through No. 6) (β-glucan content in healthy subjects: 0.2±0.3 pg/ml). In 3 of the cases (No. 1 through No. 3), *Candida albicans, Candida tropicalis* and *Cryptococcus neoformans* were respectively detected upon seroculture. In one case (No. 4), seroculture gave a negative result but *Aspergillus fumigatus* was detected upon histopathological examination at autopsy. In the remaining 2 cases (No. 5 and No. 6), seroculture gave negative results although fungal infection was strongly suspected based on clinical symptoms, courses, drug sensitivities and so on. However, administration of the antimycotic agent miconazole clinically resulted in marked improvement and therefore the patients were presumably suffering from a fungal infection.

Thus, fungal infections, in particular those profound fungal infections that are very difficult to diagnose by the conventional tests, could be diagnosed rapidly and exactly by assaying β-glucan after treatment of PRP samples from patients with fungal infection with the pretreating reagent of the present invention.

EXAMPLE 1-6

Assay of Serum Samples from Patients with Fungal Infection

Blood was collected from each of several patients suspected of fungal infection by the procedure of Example 1-3 and a serum sample was prepared therefrom. A 5-μl portion of the sample was placed in a well of Toxipet Plate 96F and 20 μl of a 0.1 mole/liter aqueous KOH solution [pretreating reagent] was further added to the well. After 10 minutes incubation at 37° C., the mixture in each well was used as a test solution. The solution was reacted with G test by the same means as used in Example 1-1 and the absorbance was measured. Using known amounts of the same reagent curdlan as used in Example 1-4 as a standard reagent, a calibration curve was separately prepared. The β-glucan content in each test solution prepared as above was determined based on said calibration curve. The results thus obtained are shown in Table 6.

TABLE 6

| | | Serum β-glucan levels in patients with opportunistic profound fungal infection | | |
|---|---|---|---|---|
| No. | Disease | Serum β-glucan | Seroculture | Clinical symptom | Outcome |
| 1 | MM | 456.4 pg/ml | (+) | Candida guilliermonoii isolated | Surviving |
| 2 | APML | 104.8 | (+) | Candida krusei isolated | Surviving |
| 3 | APML | 152.1 | (−) | Systemic aspergillosis (autopsy) | Died |
| 4 | AML | 734.8 | (−) | Improvement after fluconazole | Surviving |
| 5 | ALL | 302.8 | (−) | Improvement after amphotericin B | Surviving |

MM: Multiple myeloma; APML: Acute promyelocytic leukemia;
AML: Acute myelocytic leukemia; ALL: Acute lymphatic leukemia.

As shown in Table 6, β-glucan was detected in high concentrations in all the cases (No. 1 through No. 5) (β-glucan content in healthy subjects: 0.2±0.2 pg/ml). In two cases (No. 1 and No. 2), *Candida guilliermondii* and *Candida krusei* were respectively detected upon seroculture. In one case (No. 3), seroculture gave a negative result but *Aspergillus fumigatus* was detected upon histopathological examination at autopsy. In the remaining two cases (No. 4 and No. 5), fungal infection was strongly suspected based on clinical symptoms, courses, drug sensitivities and so on but seroculture gave negative results. However, upon administration of antimycotic agents (amphotericin B, fluconazole), marked improvement was attained clinically and therefore the patients were presumably suffering from a fungal infection.

Thus, fungal infections, in particular those profound fungal infections that are very difficult to diagnose by the conventional tests, could be diagnosed rapidly and exactly by assaying β-glucan after treatment of serum samples from patients with fungal infection with the pretreating reagent of the present invention.

EXAMPLE 1-7

Kit for β-Glucan Assay by Gelation Method (Turbidimetry)

A kit for β-glucan assay by the gelation method (turbidimetry) (for 50 samples) was constituted from the following constituent reagents:

(A) Pretreating reagent, 1.0 ml
  0.1 mole/liter aqueous NaOH solution
(B) Reagent for factor G system reaction (lyophilizate), sufficient amount
  Lyophilizate prepared by adding 15% (w/v) dextran (molecular weight: 70,000) to a *Limulus polyphemus*-derived commercial lysate (Limulus HS II Test Wako, distributed by Wako Pure Chemical Industries, Ltd.), centrifuging the mixture at 3,500 rpm for 10 minutes, admixing the supernatant with a porous cellulose gel (Cellulofine GC-200m, distributed by Seikagaku Corporation), filtering the mixture using a glass filter and lyophilizing the filtrate.
(C) Buffer for dissolving reagent for factor G system reaction and for carrying out reaction, 5.0 ml
  0.1 mole/liter Tris-hydrochloride buffer (pH 8.0)
(D) Standard β-glucan reagent (lyophilizate), sufficient amount
  Commercial curdlan (cf. Example 1-4)
(E) Distilled water (β-glucan-free) for dissolving standard β-glucan reagent, 1.0 ml
(F) Distilled water for blank test (β-glucan-free), 1.0 ml

EXAMPLE 1-8

Kit for β-Glucan Assay by Synthetic Chromogenic Substrate Method

A kit for β-glucan assay by the synthetic chromogenic substrate method (for 100 samples) was constituted from the following constituent reagents:

(A) Pretreating reagent, 2.0 ml
  0.1 mole/liter aqueous KOH solution
(B) Reagent for factor G system reaction (lyophilizate), sufficient amount
  A lyophilizate prepared by adding 15% (w/v) dextran (molecular weight: 40,000) to a *Tachypleus tridentatus*-derived lysate, cenrifuging the mixture at 3,500 rpm for 10 minutes, passing the supernatant through a nylon membrane filter with a pore size of 0.20 μm (Nalgene syringe filter, 25 mm in diameter, product of Nalge Co.), adding the effluent to an MS mixed solution (containing 0.8M magnesium chloride and 6 mM Boc-Leu-Gly-Arg-pNA) and lyophilizing the mixture.
(C) Buffer solution for dissolving reagent for factor G system reaction and for performing reaction, 5.0 ml
  0.2 mole/liter Tris-hydrochloride buffer (pH 8.0)
(D) Standard β-glucan reagent (lyophilizate), sufficient amount
  *Poria cocos*-derived β-glucan preparation (pachyman) (cf. Example 1-1)
(E) Distilled water (β-glucan-free) for dissolving standard β-glucan reagent, 2.0 ml
(F) Distilled water (β-glucan-free) for blank test, 2.0 ml

EXAMPLE 2-1

Recovery of Endotoxin added to PRP (Influence of Polybrene Concentration in Pretreating Reagent System)

Blood (2 ml) was collected from each healthy subject with heparin added in an amount of 5 units per ml of blood and centrifuged at 150×g for 10 minutes to give a platelet rich plasma (PRP).

To 190 μl of this PRP sample was added 10 μl of an aqueous solution of Escherichia coli 0111:B4-derived endotoxin preparation (2 ng/ml). After thorough mixing, the mixture was distributed in 5-μl portions into wells of an endotoxin-free microplate (Toxipet Plate 96F, a trade name of the product distributed by Seikagaku Corporation). Mixed aqueous solutions prepared by adding polybrene to an aqueous solution containing 0.1 mole/liter of KOH, 0.01 mole/liter of calcium chloride ($CaCl_2$) and 0.1% (weight/volume) of Triton X-100 to polybrene concentrations of 0.01 to 0.5% (weight/volume) were added in 20-μl portions respectively as pretreating reagent systems. The plate was incubated at 37° C. for 10 minutes in a forced air circulation type microplate reader (Well Reader SK601, a trade name of the product distributed by Seikagaku Corporation). To 25 μl of each test solution was added 100 μl of a solution of an endotoxin-specific Limulus test reagent for synthetic substrate method [Endospecy ES-200, a trade name of the product distributed by Seikagaku Corporation) (dissolved in 5.6 ml of 0.1 mole/liter Tris-hydrochloride buffer, pH 8.0), and the reaction was conducted at 37° C. for 30 minutes. The absorbance at 405 nm was measured at 15-second intervals by two-wavelength measurement with 492 nm as a reference wavelength and the rate of change in absorbance per minute (mAbs/min) was calculated (kinetic method). The measured value obtained by using distilled water (DW) in lieu of PRP and of the pretreating reagent system was used as a control and the endotoxin concentration per ml of PRP and the percent recovery of endotoxin added were calculated. In parallel, pretreatment was performed in the same manner except that a test tube was used as a container for carrying out pretreatment and that said treatment was carried out with a pretreating reagent system free of polybrene but otherwise the same in composition as that mentioned above in a constant-temperature water bath maintained at 37° C. The test solution thus treated was distributed in 25-μl portions into test tubes and the reaction was conducted at 37° C. in a constant-temperature water bath for 30 minutes. For diazo coupling, 50 μl of 0.04% (weight/volume) sodium nitrite (in 1 mole/liter hydrochloric acid), 50 μl of 0.3% (weight/volume) ammonium sulfamate and 50 μl of 0.07% (weight/volume) N-1-naphthylethylenediamine dihydrochloride (in 14% (weight/volume) N-methyl-2-pyrrolidone) were added to each tube in that order. The whole amount was transferred to a microplate, the absorbance at 545 nm was measured using a well reader, with 630 nm as a reference wavelength, and the endotoxin concentration per ml of PRP and the percent recovery were calculated (end point method). The percent recovery data for endotoxin added as obtained by the kinetic method using the microplate as containers for pretreatment and reaction while varying the polybrene concentration in the pretreating reagent system are shown in Table 7, together with the measurement results (absorbance data and endotoxin contents calculated therefrom) obtained with PRP treated under the same conditions but without addition of endotoxin. The results obtained by using test tubes as containers for pretreatment and reaction and the polybrene-free pretreating reagent system are also shown in Table 7.

TABLE 7

| Polybrene (concentration in pretreating reagent system: %) | Without endotoxin | | Recovery (%) |
|---|---|---|---|
| | mAbs/min | As endotoxin (pg/ml) | |
| 0 | 1.1 | 30 | 100 |
| 0.01 | 0.5 | 22 | 100 |
| 0.05 | 0.3 | 10 | 100 |
| 0.1 | 0 | 0 | 100 |
| 0.2 | 0 | 0 | 100 |
| 0.3 | 0.2 | 7 | 100 |
| 0.5 | 1.1 | 30 | 100 |
| 0 (*) | — | 0 | 100 |

(*): End point method using test tubes.

From the data shown in Table 7, it is found that the recovery of endotoxin added is as good as 100% irrespective of the addition of polybrene but that the calculated endotoxin level obtained without addition of endotoxin varies markedly from 0 to 30 pg/ml as a function of the polybrene concentration. The assay result obtained by the end point method where test tubes were used as containers for reaction in lieu of the microplate was 0 pg/ml. As a cause of such significant false positive reaction in the kinetic method using microplates, there may be mentioned the nonspecific turbidity increase charactertistic of the sample as occurring at the time of reaction at such a low liquid volume level as found on microplates (conversely the sample concentration being high). As a result, said turbidity increase is measured as a significant rate of change that cannot be substantially distinguished from the rate of change which depends on endotoxin. Polybrene is effective in preventing such nonspecific turbidity increase and is used generally in a concentration, in the pretreating reagent system, of 0.05 to 0.3%, preferably 0.1 to 0.2%. It is evident that, under such conditions, the true endotoxin level in PRP can be detected exactly and rapidly with good reproducibility.

EXAMPLE 2-2

Assay with PRP Samples from Patients with Infectious Disease caused by Gram-negative Bacteria The cases were 30 healthy subjects (endotoxin level: 2.42±2.9 pg/ml) and 10 patients with a severe blood disease such as leukemia suspected of septicemia caused by gram-negative bacteria or with a liver and/or bile duct disease complicated by infection. In each case, an aseptically collected, heparinized blood sample was centrifuged at 150×g and 4° C. for 10 minutes to give a PRP sample. A 5-μl portion thereof was placed in a well of Toxipet Plate 96F, 20 μl of a pretreating reagent system comprising 0.1% of Triton X-100, 0.1 mole/liter of KOH, 0.03 mole/liter of bicine (generic name; one of Good buffers; added for increasing the solubility of the pretreating reagent system; obtained from Dojin Chemical Laboratories), 0.07% of EIP (ethylenimine polymer), 0.01 mole/liter of $CaCl_2$ and 0.1% of polybrene was added to the well, and the mixture was incubated at 37° C. for 10 minutes and used as a test solution.

Endotoxin assay was conducted by the kinetic method as in Example 2-1. The results of this examples are shown in Table 8 each in terms of the endotoxin level as determined in comparison with a calibration curve separately prepared.

TABLE 8

| Sample | Endotoxin (pg/ml) |
|---|---|
| Healthy subjects (30 cases) | 2.42 ± 2.9 |
| Patients | |
| 1 | 25.5 |
| 2 | 54.2 |
| 3 | 170.3 |
| 4 | 18.5 |
| 5 | 428.5 |
| 6 | 20.0 |
| 7 | 127.4 |
| 8 | 32.1 |
| 9 | 31.5 |
| 10 | 259.7 |

Patients 1–10, in Table 8, were patients suspected to have septicemia based on seroculture, leukocyte count and other laboratory parameters, and further from clinical signs such as fever, and as assayed by the method of this invention, high levels of endotoxin were detected in all of them. The use of PPP in lieu of the above PRP also gave similar results.

It may be understood that the diagnostic method of the invention should be evaluated as a very useful technique for the rapid diagnosis of septicemia caused by gram-negative bacteria the differential diagnosis of which is very difficult to make by ordinary test methods.

EXAMPLE 2-3

Kit for Endotoxin Assay by Synthetic Chromogenic Substrate Method

A kit (for 100 samples) for endotoxin assay by the synthetic chromogenic substrate method was constituted which comprised the following constituent reagents:

(A) Pretreating reagent system, 2.0 ml
   Solution A: 0.2 mole/liter KOH, 0.2% polybrene;
   Solution B: 0.2% Triton X-100, 0.14% ethylenimine polymer, 0.02 mole/liter $CaCl_2$, 0.06 mole/liter bicine.
   Solution A and solution B are to be mixed up just prior to use.

(B) Reagent for factor C system reaction (lyophilizate), sufficient amount
   A lyophilizate containing the factor C system components prepared from a *Tachypleus trindentatus*-derived lysate by the method of Obayashi, T. et al. (vide supra) and a synthetic chromogenic substrate (Boc-Leu-Gly-Arg-pNA).

(C) Buffer solution for dissolving reagent for factor C system reaction and carrying out reaction, 5.0 ml
   0.2 Mole/liter Tris-hydrochloride buffer (pH 8.0)

(D) Standard endotoxin reagent (lyophilizate), sufficient amount
   An *Escherichia coli* 0111:B4-derived endotoxin preparation (E) Distilled water (endotoxin-free) for dissolving standard endotoxin reagent, 2.0 ml (F) Distilled water (endotoxin-free) for blank test, 2.0 ml (G) Distilled water (endotoxin-free) for preparing 0.1 mole/liter Tris-hydrochloride buffer, 5.0 ml

EXAMPLE 3-1

Recovery of β-Glucan added to PRP (Influence of Polybrene Concentration)

To 190 µl of each PRP sample prepared by the same means as used in Example 2-1 was added 10 µl of an aqueous solution of a *Poria cocos*-derived β-glucan preparation (pachyman) (4 ng/ml). After thorough mixing, the mixture was distributed in 5-µl portions into wells of a β-glucan-free microplate (Toxipet Plate 96F, a trade name of the product distributed by Seikagaku Corporation), mixed aqueous solutions prepared by adding polybrene to an aqueous solution containing 0.1 mole/liter of KOH and 0.3 mole/liter of potassium chloride (KCl) to polybrene concentration of 0.01 to 0.5% (weight/volume) were added as pretreating reagent systems in respective 20-µl portions, and the plate was incubated at 37° C. for 10 minutes in a forced air circulation type microplate reader (Well Reader SK601, a trade name of the product distributed by Seikagaku Corporation).

The amount of β-glucan was determiend in the following manner. To 25 µl of each test solution was added 100 µl of a solution of G test (lyophilized reagent for β-glucan assay by the synthetic chromogenic substrate method which contains the factor G system components and the synthetic chromogenic substrate Boc-Leu-Gly-Arg-pNA; cf. Example 1-1) in 0.1 mole/liter HEPES buffer (pH 7.6), and the reaction was allowed to proceed at 37° C. for 30 minutes. The absorbance at 405 nm was measured by two-wavelength spectrophotometry at 15-second intervals with 492 nm as a reference wavelength, and the change in absorbance per minute (mAbs/min) was calculated (kinetic assay). Using, as a control, the measured value obtained by using distilled water in lieu of PRP and of the pretreating reagent system, the β-glucan concentration per ml of PRP and the recovery of β-glucan added were calculated for each pretreating reagent system. In parallel, pretreatment was performed in a constant-temperature water bath maintained at 37° C. in the same manner except that test tubes were used as pretreatment containers and that the pretreatment reagent systems were free of polybrene but otherwise the same as those mentioned above. The pretreated test solutions were added in 25-µl portions to test tubes and the reaction was allowed to proceed at 37° C. for 30 minutes in a constant-temperature water bath. For diazo coupling, 50 µl of 0.04% (weight/volume) sodium nitrite (in 1 mole/liter hydrochloric acid), 50 µl of 0.3% (weight/volume) ammonium sulfamate and 0.07% (weight/volume) N-1-naphthylethylenediamine dihydrochloride [in 14% (weight/volume) N-methyl-2-pyrrolidone solution) were added in that order, the whole amount of the mixture was transferred to a microplate, and the absorbance at 545 nm was measured using a well reader, with the wavelength of 630 nm as a reference. The β-glucan concentration per ml of PRP and the percent recovery were then calculated for each reagent system (end point method). In Table 9, there are shown the percent recovery data for β-glucan added as obtained by the kinetic assay using microplates as containers for carrying out the pretreatment and reaction while varying the polybrene concentration in the pretreating reagent system, together with the measurement results (absorance data and β-glucan levels calculated therefrom) for the PRP samples treated under the same conditions but without addition of B-glucan. Also shown are the corresponding results for a control assay in which test tubes were used as containers for carrying out the pretreatment and reaction and in which the mixed solutions were free of polybrene.

TABLE 9

| Polybrene (concentration in pretreating reagent system: %) | Without endotoxin | | Recovery (%) |
|---|---|---|---|
| | mAbs/min | As endotoxin (pg/ml) | |
| 0 | 1.8 | 30 | 100 |
| 0.01 | 0.9 | 15 | 100 |
| 0.05 | 0.9 | 14 | 100 |
| 0.1 | 0.7 | 10 | 100 |
| 0.2 | 0.8 | 11 | 100 |
| 0.3 | 0.9 | 13 | 100 |
| 0.5 | 1.3 | 19 | 100 |
| 0 (*) | — | 10 | 100 |

(*): End point method using test tubes.

The data shown in Table 9 indicate that a $\beta$-glucan recovery as good as 100% can be obtained irrespective of the addition of polybrene but that the calculated blood $\beta$-glucan levels obtained without addition of $\beta$-glucan range from 10 to 30 pg/ml and thus the variation is very great. Judging from the assay results obtained by using test tubes as reaction containers in lieu of the microplates, said level must be 10 pg/ml. As in the case of endotoxin assay, the nonspecific turbidity increase characteristic of the samples which occurs at the time of reaction may be mentioned as a cause of such significant false positive reaction. As a result, said turbidity increase is measured as a significant rate of change, from which the rate of change depending on $\beta$-glucan cannot be substantially distinguished any more. As in Example 2-1, polybrene is effective as an additive for preventing such non-specific turbidity increase and should recommendably be used generally in a concentration, in the pretreating reagent system, of 0.05 to 0.3% preferably 0.1 to 0.2%.

EXAMPLE 3-2

Assay of PRP Samples from Patients with Fungal Infection

Blood was sampled from patients suspected of fungal infection in the same manner as in Example 2-1 and PRP samples were prepared. A 5-$\mu$l portion of each sample was placed in a well of Toxipet Plate 96F and 20 $\mu$l of a mixed solution comprising 0.1 mole/liter of NaOH, 0.3 mole/liter of NaCl and 0.2% of polybrene was added to each well, and each mixture was incubated at 37° C. for 10 minutes and then used as a test solution. Then, the reaction with G test was performed by the same means as used in Example 3-1 and the rates of change in absorbance were measured automatically. A calibration curve was separately constructed using known amounts of the same *Poria cocos*-derived $\beta$-glucan (standard reagent) as used in Example 3-1, and the $\beta$-glucan level in the test solution mentioned above was determined by reference to said curve. The results thus obtained are shown in Table 10.

TABLE 10

| | | $\beta$-Glucan levels in plasma (PRP) samples from patients with opportunistic profound fungal infection | | | |
|---|---|---|---|---|---|
| No. | Disease | Serum $\beta$-glucan | Sero-culture | Clinical symptom | Outcome |
| 1 | ALL | 403.0 pg/ml | (+) | *Candida albicans* isolated | Died |
| 2 | AML | 30.5 | (+) | *Candida tropicalis* isolated | Died |
| 3 | AIHA | 650.4 | (+) | *Cryptococcus neoformans* isolated | Surviving |
| 4 | ALL | 62.5 | (−) | Systemic aspergillosis (autopsy) | Died |
| 5 | ALL | 95.0 | (−) | Improvement after miconazole | Surviving |
| 6 | AML | 47.2 | (−) | Improvement after miconazole | Surviving |

ALL: Acute lymphatic leukemia; AML: Acute myelocytic leukemia; AIHA: Autoimmune hemolytic anemia.

As shown in Table 10, $\beta$-glucan was detected at high levels in all the cases (No. 1 through No. 6) [$\beta$-glucan level in healthy subjects (18 cases): 8.0±4.0 pg/ml]. In three of the cases (No. 1 to No. 3), *Candida albicans*, *Candida tropicalis* and *Cryptococcus neoformans* were detected, respectively, upon seroculture. In one case (No. 4), seroculture gave a negative result but, upon histopathological examination at autopsy, *Aspergillus fumigatus* was detected. In the remaining two cases (No. 5 and No. 6), fungal infection was strongly suspected based on the clinical symptoms, courses, drug sensitivities and so on but seroculture gave negative results. However, considering the fact that administration of an antimycotic (miconazole) resulted in remarkable clinical improvements, the two patients were considered to have been suffering from fungal infection. The use of PPP samples in lieu of the PRP samples mentioned above gave similar results.

Thus, fungal infections, in particular those profound fungal infections that are very difficult to diagnose by the conventional test methods, could be diagnosed rapidly and exactly by subjecting the plasma samples (PRP, PPP) from patients with fungal infection to $\beta$-glucan assay after pretreatment with the pretreating reagent system of the invention.

EXAMPLE 3-3

Assay of Serum Samples from Patients with Fungal Infection

Blood was sampled from patients suspected of fungal infection in the same manner as in Example 3-1 and serum samples were prepared. A 5-$\mu$l portion of each serum sample was placed in a well of Toxipet Plate 96F, 20 $\mu$l of a mixed solution comprising 0.1 mole/liter of KOH, 0.3 mole/liter of NaCl and 0.1% of polybrene was added to each well, and each mixture was incubated at 37° C. for 10 minutes and then used as a test solution. The reaction with G test was performed by the same means as used in Example 3-1 and the rates of change in absorbance were automatically measured. A calibration curve was separately prepared using known amounts of the same *Poria cocos*-derived $\beta$-glucan (standard reagent) as used in Example 3-1 and, by reference thereto, the $\beta$-glucan level in the above-mentioned test solution was determined. The results thus obtained are shown in Table 11.

TABLE 11

Serum β-glucan levels in patients with opportunistic profound fungal infection

| No. | Disease | Serum β-glucan | Seroculture | Clinical symptom | Outcome |
|---|---|---|---|---|---|
| 1 | MM | 475.0 pg/ml | (+) | *Candida guilliermonoii* isolated | Surviving |
| 2 | APML | 104.8 | (+) | *Candida krusei* isolated | Surviving |
| 3 | APML | 158.1 | (−) | Systemic aspergillosis (autopsy) | Died |
| 4 | AML | 750.5 | (−) | Improvement after fluconazole | Surviving |
| 5 | ALL | 345.0 | (−) | Improvement after amphotericin B | Surviving |

MM: Multiple myeloma; APML: Acute promyelocytic leukemia; AML: Acute myelocytic leukemia; ALL: Acute lymphatic leukemia.

As shown in Table 11, β-glucan was detected at high levels in all the cases (No. 1 through No. 5) [β-glucan level in healthy subjects (18 cases): 7.2±2.9 pg/ml]. In two of the cases (No. 1 and No. 2), *Candida guilliermondii* and *Candida krusei* were respectively detected upon seroculture. In one case (No. 3), seroculture gave a negative result but, upon histopathological examination at autopsy, *Aspergillus fumigatus* was detected. In the remaining two cases (No. 4 and NO. 5), seroculture gave negative results although fungal infection was strongly suspected based on the clinical symptoms, courses, drug sensitivities and so on. However, administration of antimycotic agents (amphotericin B, fluconazole) produced remarkable clinical improvements, hence these patients were considered to have been suffering from fungal infection.

Thus, fungal infections, in particular those profound fungal infections that are very difficult to diagnose by the conventional test methods, could be diagnosed rapidly and exactly by subjecting the serum samples from patients with fungal infection to β-glucan assay after pretreatment with the pretreating reagent system of the invention.

EXAMPLE 3-4

Kit for β-Glucan Assay by Gelation Method (Turbidimetry)

A kit (for 50 samples) for β-glucan assay by the gelation method (turbidimetry) was constituted which comprised the following constituent reagents:

(A) Pretreating reagent system, 1.0 ml

Aqueous solution containing 0.1 mole/liter of KOH, 0.05 mole/liter of KCl and 0.2% of polybrene (B) Reagent for factor G system reaction (lyophilizate), sufficient amount Prepared by adding 15% (w/v) dextran (molecular weight: 70,000) to a commercial *Limulus polyphemus*-derived lysate (Limulus HS II Test Wako, distributed by Wako Pure Chemical Industries, Ltd.), centrifuging the mixture at 3,500 rpm for 10 minutes, admixing the supernatant with a porous cellulose gel (Cellulofine GC-200m, distributed by Seikagaku Corporation), filtering the mixture through a glass filter, and lyophilizing the filtrate.

(C) Buffer solution for dissolving reagent for factor G system reaction and for carrying out reaction, 5.0 ml 0.1 Mole/liter HEPES buffer (pH 7.6)

(D) Standard β-glucan reagent (lyophilizate), sufficient amount

*Poria cocos*-derived β-glucan preparation (pachyman)

(E) Distilled water (β-glucan-free) for dissolving standard β-glucan reagent, 1.0 ml (F) Distilled water (β-glucan-free) for blank test, 1.0 ml

EXAMPLE 3-5

Kit for β-Glucan Assay by Synthetic Chromogenic Substrate Method

A kit (for 100 samples) for β-glucan assay by the synthetic chromogenic substrate method was constituted which comprised the following constituent reagents:

(A) Pretreating reagent system, 2.0 ml

Aqueous solution containing 0.1 mole/liter of KOH, 0.3 mole/liter of KCl and 0.1% of polybrene (B) Reagent for factor G system reaction (lyophilizate), sufficient amount Prepared by adding 15% (w/v) dextran (molecular weight: 40,000) to a *Tachypelus tridentatus*-derived lysate, centrifuging the mixture at 3,500 rpm for 10 minutes, passing the supernatant through a nylon membrane filter with a pore size of 0.20 μm (Nalgene syringe filter, 25 mm in diameter, product of Nalge Co.), adding the effluent to an MS mixed solution (containing 0.8M magnesium chloride and 6 mM Boc-Leu-Gly-Arg-pNA), and lyophilizing the mixture.

(C) Buffer solution for dissolving reagent for factor G system reaction and for carrying out reaction, 5.0 ml 0.2 Mole/liter HEPES buffer (pH 7.6)

(D) Standard β-glucan reagent (lyophilizate), sufficient amount

*Poria cocos*-derived β-glucan preparation (pachyman) (cf. Example 3-4)

(E) Distilled water (β-glucan-free) for dissolving standard-β glucan reagent, 2.0 ml (F) Distilled water (β-glucan-free) for blank test, 2.0 ml (G) Distilled water (β-glucan-free) for preparing 0.1 mole/liter HEPES buffer, 5.0 ml

EXAMPLE 4-1

Assay of PRP Samples from Infectious Disease Patients

The cases used included 18 healthy subjects, 10 patients with a severe blood disease such as leukemia suspected of septicemia caused by gram-negative bacteria or with a liver and/or bile dust disease complicated by infection, and 6 patients suspected of fungal infection. In each case, blood was sampled ascetically with heparinization and centrifuged at 4° C. and 150×g for 10 minutes to give a PRP sample. A 5-μl portion thereof was placed in a well of Toxipet Plate 96F, 20 μl of a mixed solution comprising 0.1 mole/liter of KOH and 0.1% of polybrene was added, and the mixture was incubated at 37° C. for 10 minutes and then used as a test solution.

Endotoxin assay was performed in the same manner as in Example 2-1 by the kinetic method using Endospecy. A calibration curve was constructed separately using known amounts of endotoxin (derived from *Escherichia coli* 0111:B4) as a standard reagent and, by reference thereto, the endotoxin level in the test solution was determined.

Assay of β-glucan was performed in the same manner as in Example 3-1 by the kinetic method using G test. A calibration curve was prepared separately using known amounts of a β-glucan preparation (*Poria cocos*-derived pachyman) as a standard reagent and, by reference thereto, the β-glucan level in the test solution was determined. The results thus obtained are summarized in Table 12.

TABLE 12

| Sample Patient | Endotoxin (pg/ml) |
|---|---|
| 1 | 22.7 |
| 2 | 50.8 |
| 3 | 170.0 |
| 4 | 15.9 |
| 5 | 416.8 |
| 6 | 17.5 |
| 7 | 113.3 |
| 8 | 30.9 |
| 9 | 30.5 |
| 10 | 242.8 |
| | β-Glucan (pg/ml) |
| 11 | 402.5 |
| 12 | 27.6 |
| 13 | 635.2 |
| 14 | 60.7 |
| 15 | 88.6 |
| 16 | 45.7 |

The patients No. 1 through No. 10 listed in Table 12 were cases diagnosed as being suspected of septicemia caused by gram-negative bacteria. In all of these cases, endotoxin was detected at high levels by the method of the invention endotoxin level in healthy subjects (18 cases): 2.0±2.5 pg/ml]. The use of PPP samples in lieu of the above PRP samples gave similar results.

The patients No. 11 to No. 16 listed in Table 12 were cases suspected of fungal infection but other tests failed to confirm it in every case. The above-mentioned method of the invention detected increased levels of β-glucan in all the cases [β-glucan level in healthy subjects (18 cases): 7.0±2.5 pg/ml].

When PPP samples were used in lieu of the PRP samples, similar results were obtained.

The above results thus have confirmed that both endotoxin assay and β-glucan assay can be performed using samples treated with one and the same pretreating reagent system.

As detailedly illustrated hereinabove, the present invention can provide pretreating reagents or reagent systems with which biological samples, such as blood samples, to be subjected to various biochemical reactions can be pretreated efficiently and, particularly in assaying- β-glucan in biological samples, such as plasma or serum samples, which contain factors interfering with the factor G system reaction or in assaying endotoxin in such samples which contain factors interfering with the factor C system reaction, the invention can entirely avert influences of such interfering factors on the reaction system by employing simple means comprising treating the samples with a pretreating reagent system containing an alkali metal hydroxide and a hexadimethrine compound as essential constituents thereof. At the same time, the turbidity increase in test solutions after treatment can be prevented. Furthermore, there is no need of removing any denatured product precipitate after treatment, hence the overall procedure can be curtailed. In addition, the assay method of the invention makes it possible to automatically assay endotoxin or β-glucan in biological samples on microplates by the kinetic method and thus gives highly accurate and reproducible results rapidly in a simple and easy manner. By applying the assay method of the invention to clinical testing, those profound fungal infections and infectious diseases caused by gram-negative bacteria that are very difficult to diagnose by the conventional test methods can be diagnosed rapidly and exactly.

In assaying β-glucan in biological samples, the influences, on the factor G System reaction, of factors interfering with said reaction can be entirely eliminated by treating said samples with a pretreating reagent containing an alkali metal hydroxide as an essential component thereof in accordance with the invention.

While the invention has been described in detail and with reference to specific examples thereof, it will be apparent to one skilled in the art that various changes and modifications can be made therein without departing from the spirit and scope thereof.

What is claimed is:

1. A method for pretreating a sample containing a substance detectable by a Limulus reaction together with at least one factor interfering with the Limulus reaction prior to detecting said substance utilizing said reaction which method comprises admixing a pretreating reagent comprising a hexadimethrine compound and an alkali metal hydroxide with said sample to form a mixture and incubating the mixture.

2. The method as claimed in claim 1, wherein the sample is blood-derived.

3. The method as claimed in claim 1, wherein the substance detectable by the Limulus reaction is endotoxin and wherein the pretreating reagent further comprises a nonionic or anionic surfactant and an alkaline earth metal halide.

4. The method as claimed in claim 1, wherein the substance detectable by the Limulus reaction is (1→3)-β-D-glucan and wherein the pretreating reagent further comprises an alkali metal halide.

5. A method for assaying, by utilizing a Limulus reaction, a substance present in a sample, which method comprises pretreating the sample by the method of claim 1, mixing the thus-pretreated sample with Limulus reagent, allowing a reaction to proceed and detecting the presence of said substance.

6. A method of diagnosing an infectious disease which comprises assaying for a substance occurring in a biological sample and specifically reacting with a Limulus reagent, said method comprising pretreating the biological sample by the method of claim 1, mixing the thus-pretreated sample with Limulus reagent, allowing a reaction to proceed and determining the amount of said substance relative to a standard.

7. A method for pretreating a sample containing ( 1→3)-β-D-glucan detectable by a Limulus reaction together with at least one factor interfering with said Limulus reaction prior to assaying (1→3)-β-D-glucan in said sample which comprises admixing a pretreating reagent comprising a hexadimethrine compound and an alkali metal hydroxide as main components with said sample to form a mixture and incubating the mixture.

8. A method for assaying, by utilizing a Limulus reaction, (1→3)-β-D-glucan present in a sample, which method comprises pretreating the sample by the method of claim 7, mixing the thus-pretreated sample with Limulus reagent, allowing a reaction to proceed and detecting the presence of said (1→3)-β-D-glucan.

9. A method of diagnosing a fungal-infectious disease which comprises assaying (1→3)-β-D-glucan in a biological sample, said method comprising pretreating the biological sample by the method of claim 7, mixing the thus-pretreated sample with Limulus reagent, allowing a reaction to proceed and determining the amount of said (1→3)-β-D-glucan relative to a standard.

10. An assay kit for assaying a substance specifically reacting with a Limulus reagent, which kit comprises at least the following constituent reagents:
   (A) at least one pretreating reagent comprising a hexadimethrine and an alkali metal hydroxide, and
   (B) a Limulus reagent derived from a horseshoe crab amebocyte lysate.

11. An assay kit as claimed in claim 10, wherein the Limulus reagent (B) is one specifically reacting with endotoxin and wherein the substance specifically reacting with the Limulus reagent is endotoxin.

12. An assay kit as claimed in claim 10, wherein the Limulus reagent (B) is one specifically reacting with $(1\rightarrow 3)$-$\beta$-D-glucan and wherein the substance specifically reacting with the Limulus reagent is $(1\rightarrow 3)$-$\beta$-D-glucan.

13. An assay kit as claimed in claim 11, which further comprises, as an additional constituent reagent (C) as follows:
   (C) a standard reagent containing a predetermined amount of endotoxin.

14. An assay kit as claimed in claim 12, which further comprises, as an additional constituent reagent (D) as follows:
   (D) a standard reagent containing a predetermined amount of $(1\rightarrow 3)$-$\beta$-D-glucan.

15. An assay kit for assaying $(1\rightarrow 3)$-$\beta$-D-glucan, which kit comprises at least the following constituent reagents:
   (A) a pretreating reagent comprising a hexadimethrine compound and an alkali metal hydroxide as main components, and
   (B) a Limulus reagent derived from a horseshoe crab amebocyte lysate which specifically reacts with $(1\rightarrow 3)$-$\beta$-D-glucan.

* * * * *